United States Patent
Caplan et al.

(10) Patent No.: US 11,317,868 B2
(45) Date of Patent: May 3, 2022

(54) SYSTEM AND METHOD FOR INTRAVASCULAR STRUCTURAL ANALYSIS COMPENSATION OF CHEMICAL ANALYSIS MODALITY

(71) Applicant: INFRAREDX, INC., Burlington, MA (US)

(72) Inventors: Jay D. Caplan, Belmont, MA (US); Huwei Tan, Needham, MA (US)

(73) Assignee: Infraredx, Inc., Bedford, MA (US)

( * ) Notice: Subject to any disclaimer, the term of this patent is extended or adjusted under 35 U.S.C. 154(b) by 1111 days.

(21) Appl. No.: 15/656,582

(22) Filed: Jul. 21, 2017

(65) Prior Publication Data

US 2018/0049699 A1 Feb. 22, 2018

Related U.S. Application Data

(63) Continuation of application No. 12/062,188, filed on Apr. 3, 2008, now Pat. No. 9,713,448.

(51) Int. Cl.
*A61B 5/00* (2006.01)
*A61B 8/12* (2006.01)
(Continued)

(52) U.S. Cl.
CPC .......... *A61B 5/6852* (2013.01); *A61B 5/0062* (2013.01); *A61B 5/0066* (2013.01);
(Continued)

(58) Field of Classification Search
None
See application file for complete search history.

(56) References Cited

U.S. PATENT DOCUMENTS

| | | | |
|---|---|---|---|
| 4,794,931 A | 1/1989 | Yock | |
| 5,007,428 A | 4/1991 | Watmough | |
| (Continued) | | | |

FOREIGN PATENT DOCUMENTS

| | | |
|---|---|---|
| WO | WO 1997/32182 A1 | 9/1997 |
| WO | WO 2003/057040 A1 | 7/2003 |
| (Continued) | | |

OTHER PUBLICATIONS

Pasterkamp et al., Techniques characterizing the coronary atherosclerotic plaque: influence on clinical decision making? J. Am. Coll. Cardiol. 2000, 36, 13-21.

(Continued)

*Primary Examiner* — Patricia J Park
(74) *Attorney, Agent, or Firm* — Rothwell, Figg, Ernst & Manbeck, P.C.

(57) ABSTRACT

A multimodal intravascular analysis uses a structural intravascular analysis modality to compensate for a chemical analysis modality. Examples of structural analysis are IVUS, OCT, including optical coherence domain Reflectometry (OCDR) and optical frequency domain imaging (OFDI), and/or sonar rangefinding. Examples of chemical or functional analysis are optical, NIR, Raman, fluorescence and spectroscopy, thermography and reflectometry. In one example, the structural analysis is used to characterize the environment structurally, such as catheter head-vessel wall distance. This information is then used to select from two or more algorithms which are depth specific (e.g. shallow vs. deep), to achieve improved accuracy in the chemical or functional analysis.

21 Claims, 5 Drawing Sheets

(51) Int. Cl.
*A61B 5/02* (2006.01)
*A61B 8/00* (2006.01)

(52) U.S. Cl.
CPC .......... *A61B 5/0075* (2013.01); *A61B 5/0086* (2013.01); *A61B 5/02007* (2013.01); *A61B 5/6886* (2013.01); *A61B 8/445* (2013.01); *A61B 8/4416* (2013.01); *A61B 5/0035* (2013.01); *A61B 5/0095* (2013.01); *A61B 8/12* (2013.01); *A61B 8/4461* (2013.01)

(56) References Cited

U.S. PATENT DOCUMENTS

| | | |
|---|---|---|
| 5,029,588 A | 7/1991 | Yock et al. |
| 5,293,873 A | 3/1994 | Fang |
| 5,553,610 A | 9/1996 | Lodder |
| 6,002,958 A | 12/1999 | Godik |
| 6,016,440 A | 1/2000 | Simon et al. |
| 6,254,543 B1 | 7/2001 | Grunwald et al. |
| 6,264,610 B1 | 7/2001 | Zhu |
| 6,272,411 B1 | 8/2001 | Corrado et al. |
| 6,390,978 B1 | 5/2002 | Irion et al. |
| 6,409,672 B2 | 6/2002 | Webler et al. |
| 6,501,551 B1 | 12/2002 | Tearney et al. |
| 6,507,747 B1 | 1/2003 | Gowda et al. |
| 6,690,958 B1 | 2/2004 | Walker et al. |
| 6,738,653 B1 | 5/2004 | Sfez et al. |
| 6,740,036 B1 | 5/2004 | Lee et al. |
| 6,763,261 B2 | 7/2004 | Casscells, III et al. |
| 6,815,694 B2 | 11/2004 | Sfez et al. |
| 6,921,366 B2 | 7/2005 | Jeon et al. |
| 6,949,072 B2 | 9/2005 | Furnish et al. |
| 7,144,370 B2 | 12/2006 | Fomitchov |
| 7,190,991 B2 | 3/2007 | Cable et al. |
| 7,242,480 B2 | 7/2007 | Alphonse |
| 7,268,861 B2 | 9/2007 | Treado et al. |
| 7,289,842 B2 | 10/2007 | Maschke |
| 7,450,241 B2 | 11/2008 | Zuluaga |
| 2003/0028114 A1 | 2/2003 | Casscells, III et al. |
| 2003/0199747 A1 | 10/2003 | Michlitsch et al. |
| 2003/0236443 A1 | 12/2003 | Cespedes et al. |
| 2004/0024298 A1 | 2/2004 | Marshik-Geurts et al. |
| 2005/0043637 A1* | 2/2005 | Caplan ................ A61B 5/0075 600/481 |
| 2005/0075574 A1* | 4/2005 | Furnish ................ A61B 5/0086 600/467 |
| 2005/0101859 A1 | 5/2005 | Maschke |
| 2005/0113685 A1 | 5/2005 | Maschke et al. |
| 2005/0131289 A1 | 6/2005 | Aharoni et al. |
| 2005/0228295 A1 | 10/2005 | Tan |
| 2006/0058622 A1 | 3/2006 | Tearney et al. |
| 2006/0132790 A1 | 6/2006 | Gutin |
| 2007/0043292 A1 | 2/2007 | Camus et al. |
| 2007/0066890 A1 | 3/2007 | Maschke |
| 2007/0066983 A1 | 3/2007 | Maschke |
| 2007/0078348 A1 | 4/2007 | Holman |
| 2007/0100239 A1 | 5/2007 | Nair et al. |
| 2007/0135887 A1 | 6/2007 | Maschke |
| 2007/0238953 A1 | 10/2007 | Lucassen et al. |
| 2008/0097223 A1 | 4/2008 | Strickler et al. |
| 2008/0177138 A1* | 7/2008 | Courtney .......... A61B 1/00112 600/109 |
| 2008/0177145 A1 | 7/2008 | Furnish |
| 2009/0203991 A1 | 8/2009 | Papaioannou et al. |
| 2009/0253989 A1 | 10/2009 | Caplan et al. |
| 2009/0299195 A1 | 12/2009 | Muller et al. |

FOREIGN PATENT DOCUMENTS

| | | |
|---|---|---|
| WO | WO 2003/088817 A2 | 10/2003 |
| WO | WO 2007/123518 A1 | 11/2007 |
| WO | WO 2008/057573 A2 | 5/2008 |

OTHER PUBLICATIONS

Martin et al., "An ultrasonic catheter for intravascular measurement of blood flow: Technical details" IEEE Transactions on sonics and ultrasonics, vol. SU-27, No. 6 pp. 277-286, Nov. 1980.

Römer et al., "Intravascular ultrasound combined with raman spectroscopy to localize . . . " Arterioscler Thromb Vasc Biol, 2000, vol. 20, pp. 478-483.

International Search Report, and Written Opinion for PCT Patent Application No. PCT/US2009/039449, 23 pages (dated Jun. 22, 2009).

* cited by examiner

Analysis (P1) = model {(response of P1), (distance P1)}

Analysis (P2) = model {(response of P2), (distance P2)}

SYSTEM AND METHOD FOR INTRAVASCULAR STRUCTURAL ANALYSIS COMPENSATION OF CHEMICAL ANALYSIS MODALITY

CROSS-REFERENCE TO RELATED APPLICATION

This application is a continuation claiming the benefit under 35 U.S.C. § 120 of the filing date of non-provisional patent application Ser. No. 12/062,188 filed Apr. 3, 2008, now U.S. Pat. No. 9,713,448, the disclosure of which is incorporated herein by reference

BACKGROUND OF THE INVENTION

Intravascular ultrasound (IVUS) is a medical imaging technology. It uses a specially designed catheter that includes an ultrasound transducer. In the typical application, the catheter is inserted into the vascular system of a patient and moved to an artery or vein of interest. It allows the doctor to obtain an image of the inner walls of the blood vessels, even through intervening blood. Specifically, it allows visualization of the endothelium (inner wall) of blood vessels, and structures within the vessels walls.

In its typical application, IVUS is used in coronary arteries of the heart to locate, identify and characterize atherosclerotic plaques in patients. It can be used both to determine the plaque volume in the blood vessel wall and also the degree of stenosis (narrowing) of the blood vessels. In this way, IVUS is an important technology for the structural analysis of blood vessels.

Optical coherence tomography (OCT) is an emerging technology that also provides structural information similar to IVUS. OCT also uses a catheter that is moved through the blood vessels to regions of interest. An optical signal is emitted from the catheter head and the returning signal is analyzed for phase or coherence in a Michelson interferometer, usually.

OCT has potential advantages over IVUS. Generally, OCT provides the opportunity for much higher spatial resolution, but the optical signals have limited penetration through blood and attenuate very quickly when propagating through the walls of the blood vessels.

An objective to using systems based on OCT and IVUS structural imaging technologies is the early identification of vulnerable plaques since disruption or rupture of atherosclerotic plaques appears to be the major cause of heart attacks and strokes. After the plaques rupture, local obstructive thromboses form within the blood vessels. Both venous and arterial thrombosis can occur. A coronary thrombus often initially forms at the site of rupture of a vulnerable plaque; i.e. at the location of a plaque with a lipid-rich core and a thin fibrous cap (thin-cap fibroatheroma or TCFA).

Another class of intravascular analysis systems directed to the diagnosis and analysis of atherosclerosis uses chemical analysis modalities. These approaches generally rely on optical analysis including near infrared (NIR), Raman, and fluorescence spectral analysis.

Probably the most common and well developed of these chemical analysis modalities is NIR analysis of the blood vessel walls. Similar to OCT, NIR analysis utilizes an intravascular optical catheter. In a typical application, the catheter is driven by a pullback and rotation unit that simultaneously rotates the catheter head around its longitudinal axis while withdrawing the catheter head through the region of the blood vessel of interest.

During this pullback operation, the spectral response of the inner vessel walls is acquired in a raster scan operation. This provides a spatially-resolved spectroscopic analysis of the region of interest. The strategy is that by determining the spectroscopic response of blood vessel walls, the chemical constituents of those blood vessel walls can be determined by application of chemometric analysis for example. In this way, potentially vulnerable plaques are identified so that, for example, stents can be deployed in order reduce the risk of myocardial infarction.

In Raman spectral analysis, the inner walls of the blood vessel are illuminated by a narrow band, such as laser, signal. The Raman spectral response is then detected. This response is generated by the inelastic collisions between photons and the chemical constituents in the blood vessel walls. This similarly produces chemical information for the vessel walls.

Problems associated with Raman analysis are, however, that the Raman process is a very weak and requires the use of high power optical signals in order to generate an adequate Raman response. Fluorescence has some advantages in that the fluorescence response is sometimes much larger than the Raman response. Generally, however, fluorescence analysis does not yield as much information as Raman or NIR analysis.

Another advantage of NIR analysis is that the blood flow does not necessarily have to be occluded during the analysis. The judicious selection of the wavelengths of the optical signals allows adequate penetration through intervening blood to the vessels walls and back to the catheter head.

In an effort to obtain the valuable information from both the chemical and structural analysis modalities, hybrid IVUS/optical catheters have been proposed. For example, in U.S. Pat. No. 6,949,072, a "device for vulnerable plaque detection" is disclosed. Specifically, this patent is directed to intravascular probe that includes optical waveguides and ports for the near infrared analysis of the blood vessel walls while simultaneously including an ultrasound transducer in the probe in order to enable IVUS analysis of the blood vessel walls.

SUMMARY OF THE INVENTION

The present invention concerns multimodal intravascular analysis. It uses a structural intravascular analysis modality to compensate for a chemical analysis modality. Examples of structural analysis are IVUS, OCT, including optical coherence domain Reflectometry (OCDR) and optical frequency domain imaging (OFDI), and/or sonar rangefinding. Examples of chemical or functional analysis are optical, NIR, Raman, fluorescence and spectroscopy, thermography and reflectometry. In one example, the structural analysis is used to characterize the environment, such as catheter head-vessel wall distance. This information is then used to select from two or more algorithms that are depth specific (e.g. shallow vs. deep), to achieve improved accuracy in the chemical or functional analysis.

In general, according to one aspect, the invention features a method for analyzing blood vessel walls. This method comprises advancing a catheter through blood vessels to regions of interest of blood vessel walls. A first form of energy is transmitted from the head of the catheter and detected after interaction with the blood vessel walls. A second form of energy is also transmitted and detected from the blood vessel walls. The first form of energy is used to determine a structural measure associated with the blood vessel walls. Then the blood vessel walls are analyzed using the second form of energy compensated by the determined structural measure based on the detected first form of energy.

In this way, the present invention is directed to a hybrid system that combines the use of two different analysis modalities: a first modality associated with a more structural analysis; combined with a second modality that is largely a chemical analysis modality. In this way, the structural analysis information is used to compensate or improve the information from the chemical analysis, which has the potential of providing better direct information concerning the regions of interest and whether a specific vulnerable plaque lesion is present, or not.

In one embodiment, the first form of energy is ultrasonic energy. In this way, the system has an IVUS capability. In some examples, this ultrasound signal is generated photo acoustically. In other examples, the ultrasonic energy is used in a simpler sonar rangefinding implementation. In still other examples, the first form of energy is an optical signal as used in OCT analysis.

In the preferred embodiment, the second form of energy is optical energy. Specifically, analyzing the blood vessel walls comprises using the detected optical energy to resolve the spectral response of the blood vessel walls. In examples, the NIR, fluorescence or Raman response of the blood vessels walls is obtained.

In still further examples, simply the reflectances of the blood vessel walls are detected using the second form of energy.

In one example, the first form of energy is used to select a prediction model for analyzing the detected second form of energy.

In other examples, the first form of energy is used to select thresholds for analyzing the detected second form of energy.

In implementations, the structural measure includes a physical relationship between the head of the catheter and the blood vessel walls. In other cases, it includes the thickness of a plaque of the blood vessel walls or the thickness of the blood vessel walls themselves. In this way, by determining the distance between the catheter head and the blood vessel walls using the structural analysis modality on a point-by-point basis, the chemometric analysis generated by the NIR analysis of the blood vessel walls can be compensated with this information to thereby improve the accuracy of this chemometric analysis.

Depending on the various implementations, the first form of energy and the second form of energy are transmitted simultaneously while withdrawing the catheter head through the blood vessels. In other examples, the first form of energy and the second form of energy are generated and detected during successive of pullback and rotation operations of the catheter head.

In general, according to another aspect, the invention features a system for analyzing blood vessel walls. This system comprises a catheter that is advanced through blood vessels to regions of interest of the blood vessel walls. The catheter comprises a catheter head. It houses a first energy form system that transmits a first form of energy from the head of the catheter and detects the first form of energy from the blood vessel walls and a second energy form system that transits a second form of energy from the catheter and receives the second form of energy from the blood vessel walls. A pullback and rotation system is used to simultaneously withdraw the catheter head through the blood vessels while rotating the head around a longitudinal axis. Finally, an analyzer combines the information from each of the first and second form analyses in order to improve the analysis of the blood vessel walls. Specifically, the analyzer determines a structural measure using the first form of energy and then analyzes the blood vessel walls using the detected second form of energy after compensation by the determined structural measure.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
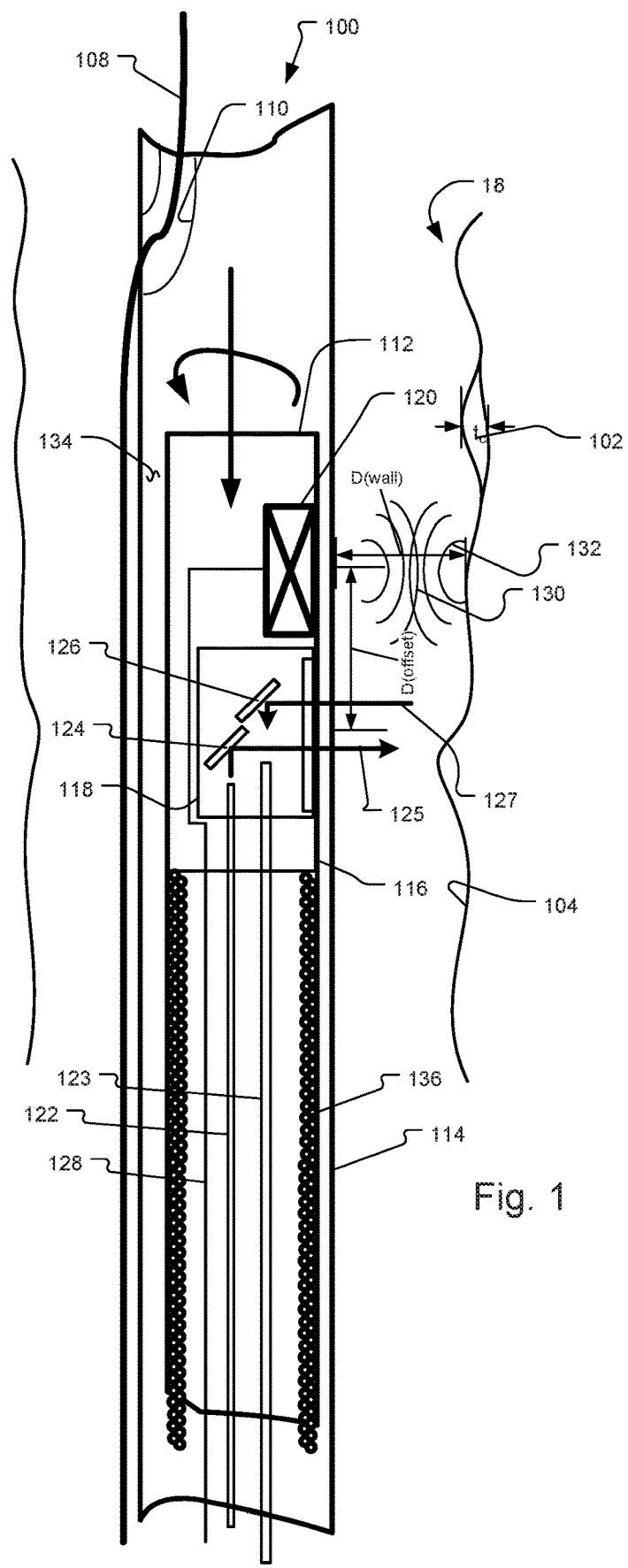
FIG. 1 is a cross-sectional view of an intravascular probe with a guidewire in a distal end of a catheter.

FIG. 1 shows an embodiment of an intravascular catheter system 100 that combines two analysis modalities based on two forms of energy: a first form of energy that yields spatially resolved structural information or even an image and a second form of energy that yields spatially resolved chemical information. Information from both sources is used to identify vulnerable plaques 102 in an arterial wall 104 of a patient. The combination of both: 1) chemical analysis modalities, using infrared spectroscopy to detect lipid content, and 2) morphometric analysis modalities, using IVUS to detect cap thickness or distance to vessel wall, enables greater selectivity in identifying potentially vulnerable plaques than either detection modality alone. These two detection modalities can achieve high sensitivity even in an environment containing blood.

In more detail, the intravascular catheter system 100 includes a guidewire lumen 110 at a distal end of the catheter system 100. In typical operation, the intravascular catheter 100 is advanced into a blood vessel 18 using guidewire 108 that is threaded through the guidewire lumen 110.

The catheter system 100 further comprises an inner scanning catheter head 112 and a sheath 114. The combination of the scanning catheter head 112 and sheath 114 enables the inner scanning catheter head 112 to perform longitudinal translation and rotation while the sheath 114 prevents this movement from damaging the vessel 18 and specifically walls 104.

At least the distal end of the sheath 114 is composed of materials that are transparent to infrared light (e.g., a polymer). The head of the scanning catheter 112 is located at the distal end of the catheter 100 and includes an optical bench 118 to transmit and receive infrared light and an ultrasound transducer 120 to transmit and receive ultrasound energy.

The optical bench 118 contains the terminations of a delivery fiber 122 and a collection fiber 123, which extend between the proximal and distal ends of the catheter 100. A light source couples light into a proximal end of the delivery fiber 122, and a delivery mirror 124 redirects light 125 emitted from a distal end of the delivery fiber 122 towards the arterial wall 104. A collection mirror 126 redirects light 127 scattered from various depths of the arterial wall 104 into a distal end of the collection fiber 123.

The ultrasound transducer system 120, which is longitudinally adjacent to the optical bench 118, includes one or more transducers that direct ultrasound energy 130 towards the arterial wall 104 and receive ultrasound energy 132 reflected from the arterial wall 104. Using time multiplexing in one implementation, a single ultrasound transducer both generates the transmitted energy 130 and transduces received energy 132 into an electrical signal carried on wires 128. For example, during a first time interval, an electrical signal carried on wires 128 actuates the ultrasound transducer 120 to emit a corresponding ultrasound signal 130. Then during a second time interval, after the ultrasound signal 130 has reflected from the arterial wall 104, the ultrasound transducer 120 produces an electrical signal carried on wires 128. This electrical signal corresponds to the received ultrasound signal 132. The received electrical signal 132 is used to reconstruct the shape of the arterial wall, including cap thickness $t_c$ of any plaque 102 and/or a distance D(wall) between the head or distal end of the scanning catheter 112 and the vessel wall 104, for example, for each spatially resolved point along the wall 104 as the head is scanned through the vessel 18.

In other embodiments, the ultrasound signal is generated photo-acoustically by sending a light pulse through optical fiber with enough energy to create an acoustic event that is detected by the IVUS transducer system 120.

Inside the sheath 114 is a transmission medium 134, such as saline or other fluid, surrounding the ultrasound transducer 120 for improved acoustic transmission. The transmission medium 134 is also selected to be transparent to the infrared light emitted from and received by the optical bench 118.

A torque cable 136 is attached to a scanning catheter housing 116 and surrounds the optical fibers 122, 123 and the wires 128. This cable 136 transmits the torque from a pullback and rotation system through to the scanning catheter head 112. This feature enables the scanning catheter head 112 to rotate within sheath 114 to circumferentially scan the arterial wall 104 with light 125 and ultrasound energy 130.

Figure 2:
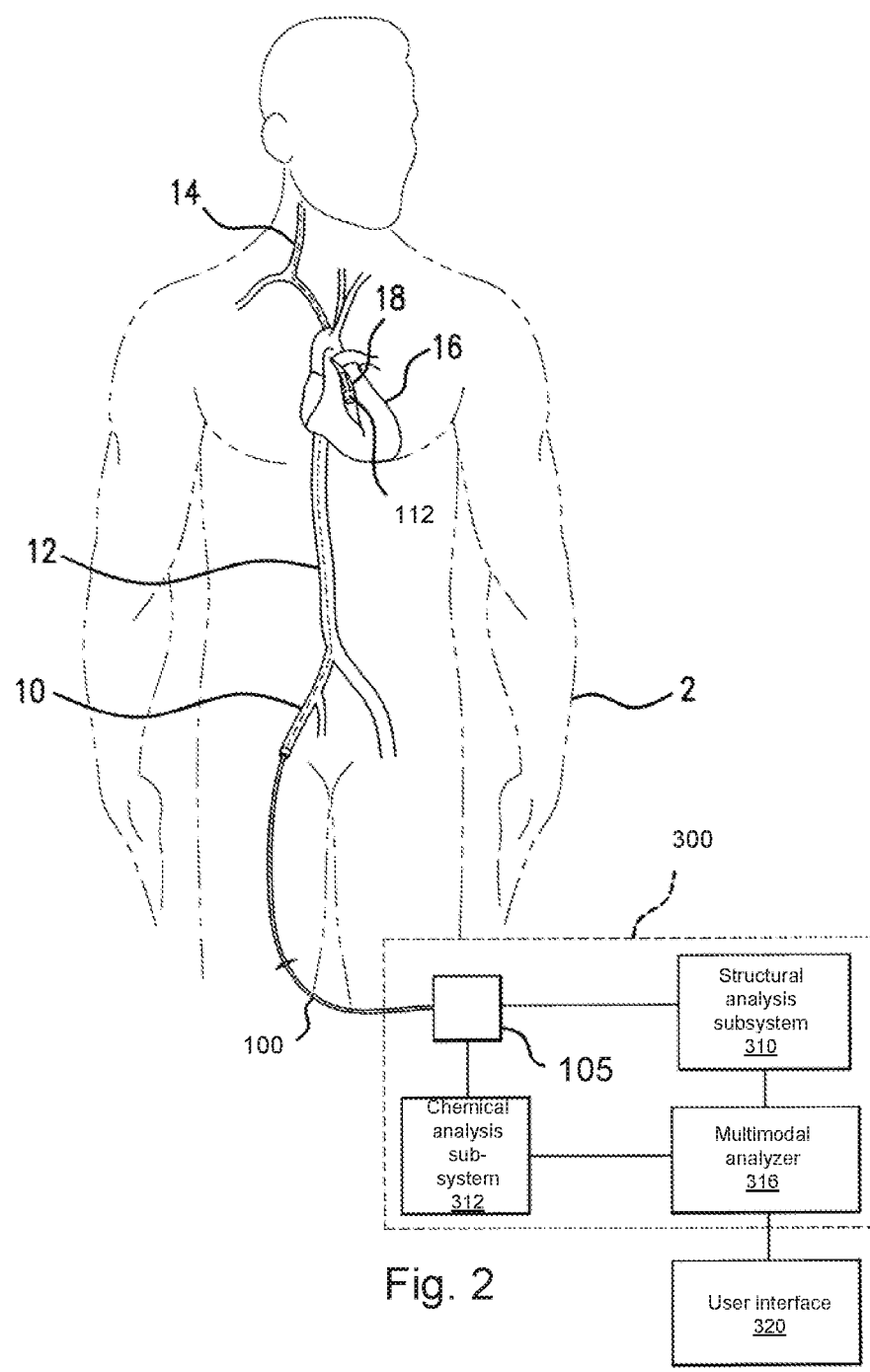
FIG. 2 is a schematic diagram illustrating the use of the catheter system and a system controller, according to the invention.

FIG. 2 illustrates an exemplary system for detecting and analyzing the spectral responses in two energy-form scanning.

The system generally comprises the catheter 100, a controller 300, and a user interface 320.

In operation, first the guide wire and then the catheter 100 are inserted into the patient 2 via a peripheral vessel, such as the femoral artery 10. The catheter head 112 is then moved to a desired target region, such as a coronary artery 18 of the heart 16 or the carotid artery 14. This is achieved by moving the catheter head 112 up through the aorta 12, riding on the guidewire.

When at the desired site, NIR radiation is generated, in one embodiment. In preferred embodiment, a tunable laser in the chemical analysis subsystem 312 generates a narrow-band optical signal that is wavelength scanned over a scan band in the NIR, covering one or more spectral bands of interest. In other embodiments, one or more broadband sources are used to access the spectral bands of interest. In either case, the optical signals are coupled into the single mode delivery fiber 122 of the catheter 100 to be transmitted to the optical bench 118.

In other examples, reflectances are measured. This is based on the discovery that lipid-rich plaques are "brighter" than other plaques, and blood is typically "darker" than tissue in the NIR. So, just a brightness measurement, corrected for blood depth, sometimes yields adequate accuracy for detection.

In the current embodiment, optical radiation in the near infrared (NIR) spectral regions is used for spectroscopy. Exemplary scan bands include 1000 to 1450 nanometers (nm) generally, or 1000 nm to 1350 nm, 1150 nm to 1250 nm, 1175 nm to 1280 nm, and 1190 nm to 1250 nm, more specifically. Other exemplary scan bands include 1660 nm to 1740 nm, and 1630 nm to 1800 nm.

However, in other optical implementations, broad band signals, other scan bands, or single frequency excitation signals appropriate for fluorescence and/or Raman spectroscopy are generated by the chemical analysis subsystem 312. In still other implementations, scan bands in the visible or ultraviolet regions are used.

In the current embodiment, the returning light is transmitted back down multimode collection fiber 123 of the catheter 100. The returning radiation is provided to the chemical analysis subsystem 312, which can comprise one or multiple optical detectors or spectrometers.

The chemical analysis subsystem 312 monitors the response of the detector, while controlling the source or tunable laser in order to resolve the spectral response of vessel walls 104 including a target area, typically on an inner wall of a blood vessel 18 and through the intervening blood or other unwanted signal sources. This spectral response is further spatially resolved as the catheter head is rotated and pulled back through the vessel 18.

As a result, the chemical analysis subsystem 312 is able to collect spectra. When the acquisition of the spectra is complete, chemical analysis subsystem 312 then provides the data to the multimodal analyzer 316.

The structural analysis subsystem 310 uses the information from the ultrasound transducer 120, in one embodiment, to generate one or more structural measures. In other examples, these structural measures are generated by an OCT, sonar rangefinding, or other structural analysis subsystem 310. The structural analysis subsystem 310 produces structural information, such as structural measures, which are also spatially-resolved with respect to the vessels as the head 112 is scanned through the vessels 18. This structural information, such as structural measures, is provided to the multi modal analyzer 316.

In more detail, the structural analysis subsystem 310 comprises the drive electronics for driving the ultrasound transducer 120 and analyzing the response of the transducer 120 to determine the structural measure of interest in a IVUS-type system. In other examples, where the second energy source is an OCT system, the structural analysis subsystem 310 is often an interferometer that resolves the phase or coherence of the light returning from the scanning catheter 112.

Generally, the analyzer 316 makes an assessment of the state of the blood vessel walls 104, which is presented to the operator via interface 320. The collected spectral response is used to determine whether each region of interest of the blood vessel wall 104 comprises a lipid pool or lipid-rich atheroma, a disrupted plaque, a vulnerable plaque or thin-cap fibroatheroma (TCFA), a fibrotic lesion, a calcific lesion, and/or normal tissue.

In should be noted that the apparent separation between the structural analysis subsystem 310, chemical analysis subsystem 312, multimodal analyzer 316, and the user interface 320 is provided to describe the various processing performed in the preferred embodiment and is thus only a notional separation in some implementations. That is, the data processing function of structural analysis subsystem 310, chemical analysis subsystem 312, multimodal analyzer 316 and the user interface 320 are performed by one a single or one or more computer systems in different implementations.

The analyzer 316 uses the structural analysis information from the structural analysis subsystem 310 to compensate information from the chemical analysis subsystem 312. Specifically, the structural analysis system produces a structural measure that is used by the multimode analyzer 316. Examples of structural measures include the instantaneous distance between the head of the catheter 112 and the blood vessels walls 104 (D(wall)) and/or the thickness of the blood vessel walls. Another structural measure is the cap thickness ($t_c$) of the lesion 102. This information is used to compensate information from the chemical analysis subsystem 312 such as serving as an input to a chemometric algorithm that has dependencies on the instantaneous or average distance between the catheter head 112 and the blood vessels walls 104. Still another structural measure is the lateral extents of plaques in the blood vessel walls.

The pullback and rotation and rotation unit 105 is used both for the mechanical drive to the scanning catheter 112 and also to couple the information or optical signals from both the IVUS and the NIR analysis portions of the catheter. Specifically, the pullback and rotation unit 105 drives the scanning catheter 112 to rotate and withdraw through the outer sheath 114.

Figure 3:
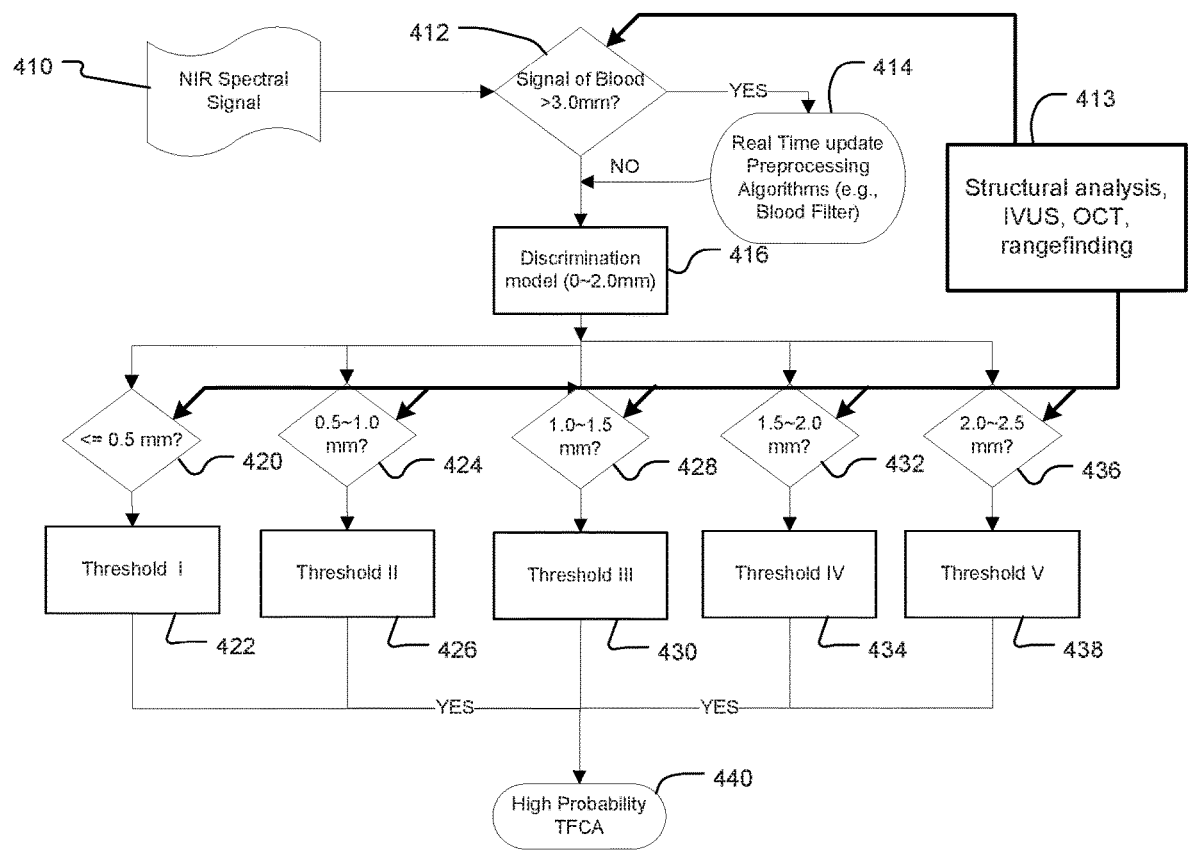
FIG. 3 is a flow diagram illustrating a method for using information from a structural analysis modality to compensate information from a chemical analysis modality, according to the invention.

FIG. 3 is a flow diagram illustrating the operation of the multimodal analyzer 316 in one embodiment.

Specifically, the NIR spectral response 410 is produced by the chemical analysis subsystem 312. Structural information 413 is further obtained from the structural analysis sub system 310.

Depending on the implementation, the structural analysis information 413 and the chemical analysis information 410 are produced during the same or different scans of the scanning catheter 112. For example, in one implementation, the chemical analysis information 410 produced by the NIR analysis and structural information 413 produced by the IVUS analysis are captured simultaneously while withdrawing and rotating the scanning catheter 112 through the blood vessels 104. In other implementations, the chemical analysis information 410 produced by the NIR analysis and structural information 413 produced by the IVUS analysis are captured during different pullback and rotation operations of the scanning catheter 112. Then the chemical analysis information 410 data set produced by the NIR analysis and structural information 413 data set are spatially aligned with respect to each other. This alignment includes compensation for the offset distance D(offset) between the IVUS transducer 120 and the optical bench 118, see FIG. 1.

This structural information is used in step 412 to determine whether or not the instantaneous, i.e., spatially resolved, NIR spectral signal was obtained from a distance of greater than 3 millimeters between the head of the scanning catheter 112 and the blood vessel wall 104.

If the distance was greater than 3 millimeters, then a real time update is performed on preprocessing algorithms. In one example, such preprocessing algorithms are described in U.S. Patent Publication Number is US 2004/0024298-A1, Publication Date Feb. 5, 2004, entitled Spectroscopic Unwanted Signal Filters for Discrimination of Vulnerable Plaque and Method Therefor. This application is incorporated herein by this reference in its entirety. Specifically, these preprocessing algorithms process the near infrared information differently depending upon the distance between the catheter head 112 and the blood vessel wall 104 when the information was obtained.

In step 416, a discrimination model is selected based upon the 0 to 2 millimeters distance. The prior preprocessing step corrects dataset generated at greater than 3.0 mm such that they can not be analyzed with a discrimination model based on 0-2 mm distances.

In more detail, one of five thresholds 422, 426, 430, 434, 438 is applied based upon a more the precise determination of the distance between the catheter head 112 and the blood vessel walls 104 produced by the structural analysis 413. That is, for each location along the vessel wall, the corresponding NIR data are processes according to the distance between the catheter head 112 and the wall when the data were obtained by reference to the structural analysis information 413. In the examples, the granularity for the different thresholds is less than 0.5 mm (step 420), 0.5-1.0 mm (step 424), 1.0-1.5 mm (step 428), 1.5-2.0 mm (step 432), and 2.0-2.5 mm (step 436). The data at each location along the wall is then processed using a separate one of the one of five thresholds 422, 426, 430, 434, 438.

Thus, based upon the distance between the catheter head 112 and the vessel wall 104 when each NIR spectral signal is obtained, a different threshold is applied. The application of the threshold is used to determine whether or not there is a high probability of a thin cap atheroma or not, in one example in step 440.

Figure 4:
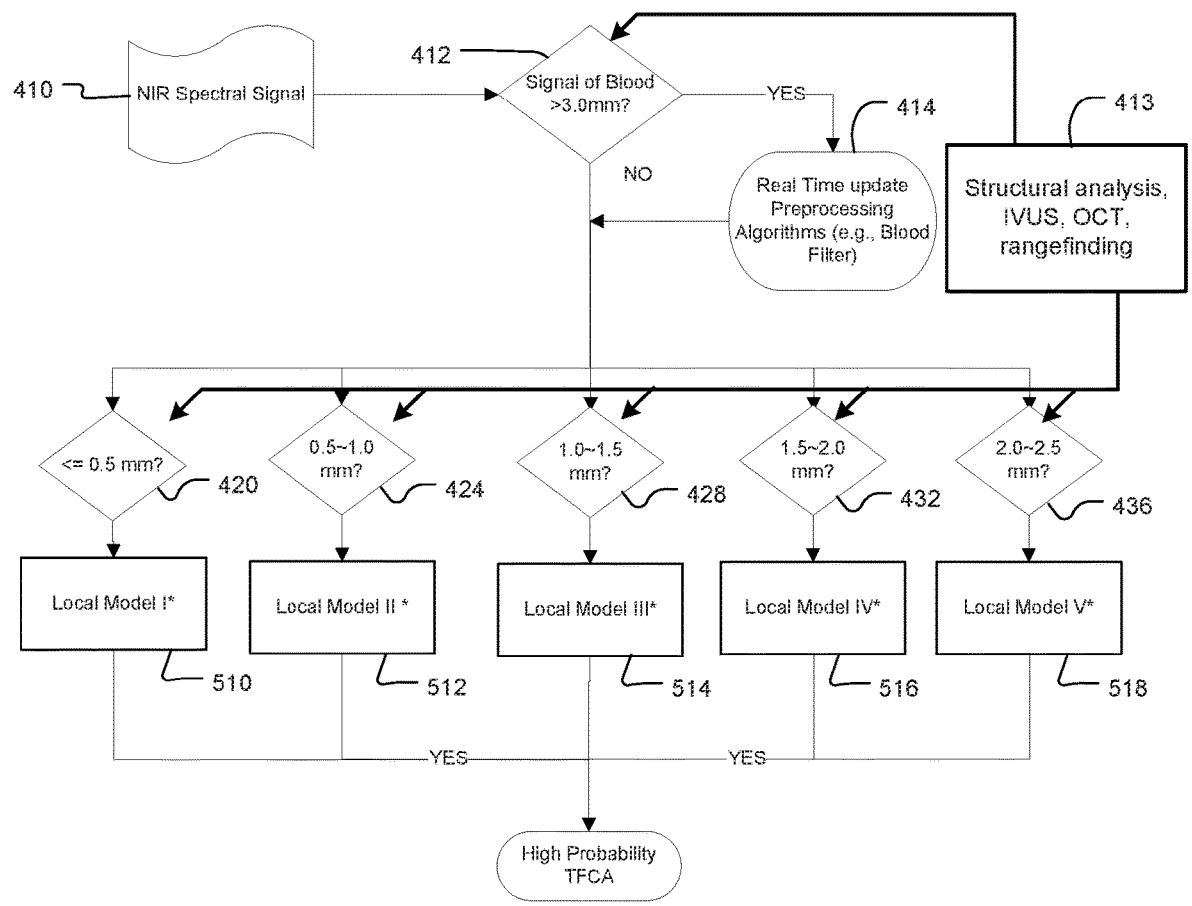
FIG. 4 is a flow diagram illustrating another method for using information from a structural analysis modality to compensate information from a chemical analysis modality, according to the invention.

FIG. 4 shows an alternative embodiment. This similarly uses preprocessing if the blood distance is greater than 3 millimeters in step 414. Then based upon the distance between the catheter head and the vessel walls when the data were obtained, different local models are applied in steps 510, 512, 514, 516, 518. These are chemometric models that are used to assess the NIR spectral signal 410.

Here, IVUS blood depth information is used to improve prediction accuracy. Different chemometric prediction models 510, 512, 514, 516, 518 are built for different blood depths: less than 0.5 mm (step 420), 0.5-1.0 mm (step 424), 1.0-1.5 mm (step 428), 1.5-2.0 mm (step 432), and 2.0-2.5 mm (step 436).

In some examples, the blood depths are determined "manually". The user inputs the blood depth after measuring the IVUS image.

In other examples, NIR prediction models are augmented with the IVUS blood depth information.

Figure 5:
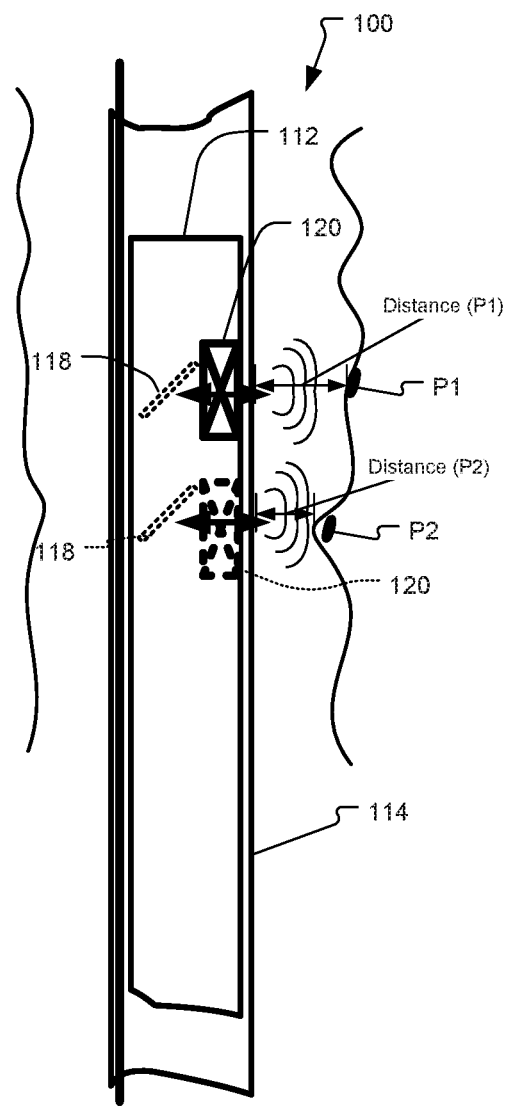
FIG. 5 is a schematic diagram illustrating the point by point method for chemometric model compensation according to the invention.

FIG. 5 illustrates still another embodiment of the invention. Specifically, this illustrates that the point-by-point NIR analysis (Analysis (Pn)) of the blood vessels walls is compensated in each case by the instantaneous information from the IVUS or first energy form (distance Pn). In this way, adjacent points in the scan of the inner walls and their different NIR responses, (response of P1) and (response of P2), are combined with the instantaneous distance to the vessel walls, (distance P1) and (distance P2) when the NIR signal data 310 was obtained to obtain distance compensated analyses Analysis (P1) and Analysis (P2). In this way, the first energy form information is used at a very high level of granularity in order to compensate the NIR spectral signal information at the spatial resolution of the chemical and/or structural analysis modality.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for analyzing blood vessel walls, the system comprising:
    a catheter configured to be advanced through blood vessels to a region of interest of the blood vessel wall while transmitting ultrasound signals to the blood vessel wall and receiving ultrasound signals reflected from the blood vessel wall and while transmitting optical energy to the blood vessel wall and receiving optical energy reflected from the blood vessel wall; and
    a controller coupled to the catheter, wherein the controller comprises:
    a structural analysis subsystem generating structural information at the region of interest of the blood vessel wall from the ultrasound signals reflected from the blood vessel wall and received by the catheter;
    a chemical analysis subsystem providing chemical analysis information of the region of interest of the blood vessel wall from the optical energy reflected from the blood vessel wall and received by the catheter; and
    a multimodal analyzer configured to compensate the chemical analysis information from the chemical analysis subsystem based on the structural information from the structural analysis subsystem to make an assessment of the state of the blood vessel wall at the region of interest based on the compensated chemical analysis information.

2. The system of claim 1, wherein the structural analysis subsystem comprises an ultrasound transducer disposed within the catheter.

3. The system of claim 1, wherein the structural information generated by the structural analysis subsystem comprises one or more of distance between the catheter and the blood vessel wall at the region of interest, thickness of the blood vessel wall at the region of interest, and cap thickness of a lesion on the blood vessel wall.

4. The system of claim 1, wherein the chemical analysis subsystem comprises an optical bench disposed within the catheter for transmitting optical energy to the blood vessel wall and receiving optical energy reflected from the blood vessel wall.

5. The system claim 4 wherein the optical bench comprises:
    distal ends of a delivery fiber and a collection fiber which extend between proximal and distal ends of the catheter;
    a delivery mirror configured to redirect light emitted from the distal end of the delivery fiber towards the blood vessel wall, and
    a collection mirror configured to redirect light scattered from the blood vessel wall into the distal end of the collection fiber.

6. The system of claim 1, wherein the chemical analysis subsystem analyzes the blood vessel walls by determining Raman spectral responses of the blood vessel wall from detected optical signals, by spatially resolving spectral responses of the blood vessel wall from detected optical signals, by determining reflectance of the blood vessel wall from detected optical signals, or by determining fluorescence responses of the blood vessel wall from detected optical signals.

7. The system of claim 1, wherein the chemical analysis subsystem analyzes the blood vessel walls by resolving spectral responses of the blood vessel walls to generate spectral data and using the spectral data to perform chemometric analysis of the blood vessel walls.

8. The system of claim 1, further comprising a pullback and rotation system for simultaneously withdrawing the catheter through the blood vessels and rotating the catheter around its longitudinal axis.

9. The system of claim 1, wherein the multimodal analyzer compensates the chemical analysis information from the chemical analysis subsystem based on a compensation technique selected from a group of techniques comprising: using the structural information from the structural analysis subsystem as an input to a chemometric algorithm, performing an update on a preprocessing algorithm based on distance to the vessel wall, selecting a discrimination model based on distance to the vessel wall, selecting at least one threshold based on distance to the vessel wall, and selecting a chemometric prediction model based on distance between the catheter and the vessel wall.

10. The system of claim 1, wherein the structural analysis subsystem generates structural information by intravascular ultrasound using photoacoustically generated ultrasound from optical energy transmitted through the catheter.

11. A system for processing data signals from an intravascular catheter to analyze a blood vessel wall, the system comprising:
    a structural analysis subsystem receiving ultrasound signals from the catheter and generating structural information relating to the blood vessel wall from the received ultrasound signals;
    a chemical analysis subsystem receiving optical signals from the catheter and generating chemical analysis information relating to the blood vessel wall from the received optical signals; and
    a multimodal analyzer configured to compensate the chemical analysis information from the chemical analysis subsystem based on the structural information from the structural analysis subsystem to make an assessment of the state of the blood vessel wall based on the compensated chemical analysis information.

12. The system of claim 11, wherein the structural analysis subsystem comprises drive electronics for driving an ultrasound transducer in the catheter and analyzing a response of the transducer to determine the structural information.

13. The system of claim 11, wherein the chemical analysis subsystem comprises a tunable laser coupled into an optical fiber of the catheter.

14. The system of claim 11, wherein the chemical analysis subsystem comprises one or multiple optical detectors or spectrometers.

15. The system of claim 11, wherein the structural information generated by the structural analysis subsystem comprises one or more of distance between the catheter and the blood vessel wall at the region of interest, thickness of the blood vessel wall at the region of interest, and cap thickness of a lesion on the blood vessel wall.

16. The system of claim 11, wherein the chemical analysis subsystem analyzes the blood vessel wall by determining Raman spectral responses of the blood vessel wall from the optical signals, by spatially resolving spectral responses of the blood vessel wall from the optical signals, by determining reflectance of the blood vessel wall from the optical signals, or by determining fluorescence responses of the blood vessel wall from the optical signals.

17. The system of claim 11, wherein the chemical analysis subsystem analyzes the blood vessel wall by resolving spectral responses of the blood vessel wall to generate spectral data and uses the spectral data to perform chemometric analysis of the blood vessel walls.

18. The system of claim 11, further comprising a pullback and rotation system configured to be coupled to the catheter and to simultaneously withdraw the catheter through the blood vessel and rotate the catheter around its longitudinal axis.

19. The system of claim 11, wherein the multimodal analyzer compensates the chemical analysis information from the chemical analysis subsystem based on a compensation technique selected from a group of techniques comprising: using the structural information from the structural analysis subsystem as an input to a chemometric algorithm, performing an update on a preprocessing algorithm based on distance to the vessel wall, selecting a discrimination model based on distance to the vessel wall, selecting at least one threshold based on distance to the vessel wall, and selecting a chemometric prediction model based on distance between the catheter and the vessel wall.

20. The system of claim 1, wherein the chemical analysis subsystem analyzes the blood vessel walls by resolving spectral responses of the blood vessel walls to generate spectral data and by using the spectral data to perform chemometric analysis of the blood vessel walls to generate the chemical analysis information.

21. The system of claim 1, wherein the optical energy comprises near infrared, fluorescence, or Raman.

* * * * *